United States Patent [19]

Witt et al.

[11] Patent Number: 5,001,286

[45] Date of Patent: Mar. 19, 1991

[54] PROCESS FOR SEPARATING SULPHURIC ACID AND NITRIC ACID FROM DINITROTOLUENE MIXTURES OBTAINED DURING THE NITRATION OF TOLUENE

[75] Inventors: Harro Witt, Kuden; Heiko Beckhaus, Leverkusen, both of Fed. Rep. of Germany

[73] Assignee: Bayer Aktiengesellschaft, Leverkusen, Fed. Rep. of Germany

[21] Appl. No.: 155,199

[22] Filed: Feb. 12, 1988

[30] Foreign Application Priority Data

Feb. 18, 1987 [DE] Fed. Rep. of Germany ....... 3705091

[51] Int. Cl.$^5$ ............................................ C07C 205/08
[52] U.S. Cl. ..................................... 568/934; 568/932; 568/939; 568/940
[58] Field of Search ................ 568/934, 932, 939, 940

[56] References Cited

U.S. PATENT DOCUMENTS

| 2,012,985 | 9/1935 | Castner | 568/934 X |
| 2,401,879 | 6/1946 | McKee | 568/935 |
| 3,157,706 | 11/1964 | Ozeki et al. | 568/934 |
| 3,185,738 | 5/1965 | Cossaboon et al. | 568/932 |
| 3,221,064 | 11/1965 | Brogden et al. | 568/934 |
| 3,243,466 | 3/1966 | Brodgen et al. | 568/934 |
| 3,350,466 | 10/1967 | Menke | 568/934 |
| 3,434,802 | 3/1969 | Toischer et al. | 422/189 |
| 4,482,769 | 11/1984 | Toseland et al. | 568/934 |
| 4,496,782 | 1/1985 | Carr | 568/934 |
| 4,597,875 | 7/1986 | Carr et al. | 210/710 |

OTHER PUBLICATIONS

Kirk–Othmer, Encyclopedia of Chemical Technology, 2nd Edition, vol. 13, p. 844 et seq.

*Primary Examiner*—Robert L. Stoll
*Assistant Examiner*—Valerie Fee
*Attorney, Agent, or Firm*—Joseph C. Gil; Richard E. L. Henderson

[57] ABSTRACT

Sulphuric and nitric acids present in dinitrotoluene are separated from the dinitrotoluene by adding up to 10 wt. % water (based on quantity of dinitrotoluene) to the mixture of dinitrotoluene, sulphuric acid and nitric acid, mixing and separating the aqueous phase containing nitric and sulphuric acids. The mixtures treated by this process generally contain up to 5 wt. % nitric acid and up to 6 wt. % sulphuric acid.

3 Claims, No Drawings

PROCESS FOR SEPARATING SULPHURIC ACID AND NITRIC ACID FROM DINITROTOLUENE MIXTURES OBTAINED DURING THE NITRATION OF TOLUENE

BACKGROUND OF THE INVENTION

The present invention relates to a process for separating sulphuric acid and nitric acid from dintrotoluene mixtures.

A generally employed process for the production of dinitrotoluene involves nitrating toluene in a first stage with nitric acid in the presence of sulphuric acid (mixed acid), separating the mononitrotoluenes obtained from the reaction mixture and then further nitrating them with mixed acid in a second stage to form dinitrotoluenes (See for example Kirk-Othmer, Encyclopedia of Chemical Technology, 2nd Edition, Vol. 13, p 844 et seq). The crude dinitrotoluene mixture obtained after separation of the mixed acid contains further fractions of dissolved or finely dispersed nitric acid and sulphuric acid. In the known processes, this crude dinitrotoluene mixture is washed with water in a suitable apparatus, optionally with addition of bases, and the acid residues pass into the washing water and therefore into the waste water.

SUMMARY OF THE INVENTION

It is an object of the present invention to provide a process for separating sulphuric acid and nitric acid from dinitrotoluene.

This and other objects which will be apparent to those skilled in the art are accomplished by adding up to 10 wt. % water (based on the quantity of dinitrotoluene) to a mixture of up to 6 wt. % of sulphuric acid, up to 5 wt. % nitric acid and dinitrotoluene, mixing thoroughly and separating the aqueous phase.

DETAILED DESCRIPTION OF THE INVENTION

The present invention relates to a process for separating sulphuric acid and nitric acid from dinitrotoluenes obtained during the dinitration of toluene with mixed acid which contain sulphuric acid and nitric acid. The dinitrotoluenes which are obtained after separation of the majority of sulphuric acid and nitric acid, which still contain up to 6 wt. % of sulphuric acid and up to 5 wt. % of nitric acid are mixed with up to 10 wt. % of water (based on the quantity of dinitrotoluenes). The aqueous phase containing sulphuric and nitric acid which subsequently settles is then separated.

Depending upon the type of nitration process employed, the temperature of the crude dinitrotoluene mixture and the concentration of the mixed acid used in the second nitration stage, sulphuric acid can be dissolved or finely dispersed in a quantity of up to about 6 wt. % and nitric acid can be dissolved or finely dispersed in a quantity of up to about 5 wt. % in the crude dinitrotoluene isomer mixture which contains about 76 to 77 wt. % of 2,4-dinitrotoluene, 18 to 19 wt. % of 2,6-dinitrotoluene, 1.3 to 1.7 wt. % of 2,3-dinitrotoluene, 2.1 to 2.8% of 3,4-dinitrotoluene and 0.4 to 0.8 wt. % of 2,5-dinitrotoluene. The sulphuric acid and nitric acid can be substituted for one another in part, i.e. the higher the concentration of one acid, the lower that of the other.

About 1 to 3 wt. % of sulphuric acid and 1 to 2 wt. % of nitric acid are preferably dissolved or finely dispersed in the crude dinitrotoluene mixture.

To separate and recover the sulphuric and nitric acid contained in the crude dinitrotoluene mixture, the crude dinitrotoluene mixture is mixed according to the invention with up to 10 wt. % of water, preferably from 0.3 to 8 wt. % of water, based on the quantity of dinitrotoluene.

The small quantity of added water ensures that the acid phase which settles out after the mixing process is sufficiently concentrated to be recirculated into the first nitration stage. The recirculated acid phase can thus be used again as mixed acid in the first nitration stage without special reconcentration.

In the process of the present invention, the water added to the crude dinitrotoluene mixture is mixed intensively with the dinitrotoluenes. Any conventional mixer units such as mixing pumps which at the same time have the advantage of conveying the reaction medium (e.g., stirrer-equipped containers, mixing nozzles, jet dispersers, static mixers and similar apparatus) are suitable for the mixing process.

The dinitrotoluenes are mixed with water at temperatures from about 65° to 90° C., preferably at 65° to 85° C.

In addition to the single-stage separation of sulphuric acid and nitric acid from the crude dinitrotoluene mixture, it is also possible in the practice of the present invention to separate sulphuric acid and nitric acid from the dinitrotoluene mixture in two or more stages. If separation is carried out in two stages, the dinitrotoluenes can initially be mixed with about 0.3 to 3 wt. %, preferably 0.5 to 1 wt. % of water, based on the quantity of dinitrotoluene. The heavy aqueous phase containing predominantly sulphuric acid which separates out can be run off and the organic phase containing the dinitroluenes can then be mixed with about 2 to 8 wt. %, preferably 2 to 6 wt. % water, based on the quantity of dinitrotoluene. The lighter aqueous phase containing predominantly nitric acid which separates out can be run off. Even with this two-stage process for the separation of sulphuric acid and nitric acid, it is possible to add the acid phases back into the first stage of nitration without prior reconcentration.

The advantages of the process according to the invention reside in the fact that it is possible to recover the residual quantities of sulphuric acid and nitric acid present in the crude dinitrotoluene mixture in a form which allows recycling into the nitration process. In this way, the consumption of nitric acid and sulphuric acid during the production of dinitrotoluene can be considerably reduced. At the same time, the nitrate and sulphate charge in the waste water is lowered to up to 5 wt. %, depending on the mode of operation, so that environmental pollution by sulphates and nitrates is considerably reduced.

The following Examples demonstrate the process according to the invention in more detail. All percentages in the Examples relate to percentages by weight.

EXAMPLES

EXAMPLE 1

2,600 kg/h of crude dinitrotoluene (DNT) were reacted continuously with 180 kg/h (about 7%) of completely desalinated water in a 500 l container at 70° C. The mixture was circulated by a centrifugal pump via a static mixer and was then supplied to a coalescing filter. The coalescing filter simultaneously served as a horizontal separating bottle. The acids (sulphuric acid and nitric acid) settled as aqueous phase and ran out into a pumping system. From there, they were recirculated together with mixed acid recovered from the second nitration stage into the first nitration stage. The dinitrotoluene running out as heavier organic phase was supplied to the dinitrotoluene washing device.

The crude dinitrotoluene had the following isomeric composition:

| | |
|---|---|
| 2,4-dinitrotoluene | 77.46% |
| 2,6-dinitrotoluene | 18.64% |
| 3,4-dinitrotoluene | 2.19% |
| 2,3-dinitrotoluene | 1.16% |
| 2,5-dinitrotoluene | 0.55% |

It was contaminated by traces of mononitrotoluene, trinitrotoluene and nitrocresols.

Before being mixed with water, the crude dinitrotoluene contained 1.07% of nitric acid and 5.15% of sulphuric acid.

After leaving the coalescing filter, the concentrations in the dinitrotoluene were reduced to 0.3% of nitric acid and 0.21% of sulphuric acid. This represented a reduction in the waste water charges of about 72% in the case of nitric acid and about 96% in the case of sulphuric acid.

EXAMPLE 2

4,000 kg/h of crude dinitrotoluene at a temperature of 70° C. were continuously reacted in a 500 l container with about 33 kg/h (about 0.8% by weight) of completely desalinated water. The mixture was circulated via a static mixer and was subsequently conveyed into a horizontal coalescing filter which simultaneously served as separating bottle. The heavier aqueous phase which contained predominantly sulphuric acid ran out into a pumping system. From there, it was recirculated into the first nitration stage together with the mixed acid recovered from the second nitration stage.

The dinitrotoluene leaving the separator as lighter phase was renewed, as mentioned above, reacted with 120 kg/h of completely desalinated water (about 3% by weight) and conveyed via a static mixer into a further coalescing filter. The now lighter phase containing predominantly nitric acid also ran out into the above-mentioned pumping system. From there, the lighter aqueous phase was returned to the first nitration stage. The dinitrotoluene mixture settling as heavier organic phase was supplied to a dinitrotoluene washing device. The crude dinitrotoluene mixture used corresponded in its composition to the dinitrotoluene mixture from Example 1. It contained 1.32% of nitric acid and 4.71% of sulphuric acid. After leaving the coalescing filter, the concentration had dropped to 0.52% of nitric acid and 0.15% of sulphuric acid. This represented a reduction of nitrate charge in the waste water of more than 60% and of the sulphate charge of more than 96%. Only 55% of the quantity of water employed in Example 1 was used.

EXAMPLE 3

1 kg/h of completely desalinated water at 80° C. was squirted continuously into a stream of 130 kg/h of crude DNT at 80° C. via a nozzle having a diameter of 0.1 mm. The pressure difference over the nozzle was 20 bar. The mixture formed was conveyed into a coalescing filter. The residence time of the mixture before it was separated was about 20 seconds. After separation, a heavier acid phase was removed. The lighter DNT phase was continuously reacted with 5 kg/h of water over a second nozzle having a diameter of 0.2 mm and was conveyed into a second coalescing filter. The pressure difference over the nozzle was 15 bar. The residence time was the same as in the first stage. After separation, a lighter acid phase and a heavier DNT phase ran out. The separated acid phases were recirculated into the first stage of nitration.

The crude DNT contained 1.5% of $H_2SO_4$ and 1.3% of $HNO_3$. The DNT running out after the second stage still contained 0.3% of $H_2SO_4$ ( $-77\%$) and 0.6% of $HNO_3$ ( $-54\%$).

Overall, only 4.6% of water, based on the crude DNT, was used with very short residence times.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for separating dinitrotoluene from a dinitrotoluene mixture containing up to 6 wt. % sulphuric acid and up to 5 wt. % nitric acid, wherein said dinitrotoluene mixture is obtained using a two-step nitration of toluene with a mixed acid containing sulphuric acid and nitric acid and a subsequent separation of a phase consisting essentially of said dinitrotoluene mixture from the majority of mixed acid remaining after said nitration, comprising
   (a) mixing the dinitrotoluene mixture with up to 10 wt. % water, based on the quantity of the dinitrotoluene mixture, at a temperature of from about 65° C. to about 90° C.;
   (b) allowing an aqueous phase containing sulphuric acid and nitric acid to separate;
   (c) removing said aqueous phase, thereby yielding dinitrotoluene; and
   (d) recirculating said aqueous phase as a component of said mixed acid in the first step of a subsequent two-step nitration of toluene.

2. The process of claim 1 wherein the dinitrotoluene mixture is mixed with from 0.3 to 8 wt. % water, based on the quantity of the dinitrotoluene mixture.

3. The process of claim 1 wherein the dinitrotoluene mixture is mixed with from 0.3 to 8 wt. % water, based on the quantity of the dinitrotoluene mixture; the dinitrotoluene obtained in step (c) is mixed with from 2 to 6 wt. % water, based on the quantity of the dinitrotoluene, and allowed to separate into a second aqueous phase; and the second aqueous phase is removed, thereby yielding dinitrotoluene.

* * * * *